United States Patent
Thomas et al.

(10) Patent No.: US 7,932,278 B2
(45) Date of Patent: Apr. 26, 2011

(54) 2-AMINOETHOXYACETIC ACID DERIVATIVES AND THEIR USE

(75) Inventors: Christian R. Thomas, Wuppertal (DE); Susanne Röhrig, Hilden (DE); Elisabeth Perzborn, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 403 days.

(21) Appl. No.: 11/992,396

(22) PCT Filed: Sep. 14, 2006

(86) PCT No.: PCT/EP2006/008949
§ 371 (c)(1),
(2), (4) Date: Jun. 20, 2008

(87) PCT Pub. No.: WO2007/036306
PCT Pub. Date: Apr. 5, 2007

(65) Prior Publication Data
US 2009/0036504 A1 Feb. 5, 2009

(30) Foreign Application Priority Data
Sep. 23, 2005 (DE) .......................... 10 2005 045 518

(51) Int. Cl.
*A61K 31/422* (2006.01)
*A61P 7/02* (2006.01)
*C07D 263/08* (2006.01)

(52) U.S. Cl. ....................................... 514/376; 548/229
(58) Field of Classification Search ........................ None
See application file for complete search history.

(56) References Cited

U.S. PATENT DOCUMENTS

| | | | |
|---|---|---|---|
| 2,811,555 A | 10/1957 | Larive et al. |
| 3,279,880 A | 10/1966 | Straley et al. |
| 4,128,654 A | 12/1978 | Fugitt et al. |
| 4,250,318 A | 2/1981 | Dostert et al. |
| 4,327,725 A | 5/1982 | Cortese et al. |
| 4,500,519 A | 2/1985 | Lormeau et al. |
| 4,705,779 A | 11/1987 | Madi-Szabo et al. |
| 4,765,989 A | 8/1988 | Wong et al. |
| 4,948,801 A | 8/1990 | Carlson et al. |
| 4,977,173 A | 12/1990 | Brittelli et al. |
| 5,002,937 A | 3/1991 | Bosies et al. |
| 5,254,577 A | 10/1993 | Carlson et al. |
| 5,349,045 A | 9/1994 | Jiang |
| 5,532,255 A | 7/1996 | Raddatz et al. |
| 5,561,148 A | 10/1996 | Gante et al. |
| 5,565,571 A | 10/1996 | Barbachyn et al. |
| 5,654,428 A | 8/1997 | Barbachyn et al. |
| 5,654,435 A | 8/1997 | Barbachyn et al. |
| 5,688,792 A | 11/1997 | Barbachyn et al. |
| 5,756,732 A | 5/1998 | Barbachyn et al. |
| 5,792,765 A | 8/1998 | Riedl et al. |
| 5,801,246 A | 9/1998 | Barbachyn et al. |
| 5,827,857 A | 10/1998 | Riedl et al. |
| 5,910,504 A | 6/1999 | Hutchinson et al. |
| 5,922,708 A | 7/1999 | Riedl et al. |
| 5,929,248 A | 7/1999 | Barbachyn et al. |
| 5,935,724 A | 8/1999 | Spillman et al. |
| 5,972,947 A | 10/1999 | Tsaklakidis et al. |
| 5,977,373 A | 11/1999 | Gadwood et al. |
| 5,998,406 A | 12/1999 | Hester et al. |
| 6,069,160 A | 5/2000 | Stolle et al. |
| 6,159,997 A | 12/2000 | Tsujita et al. |
| 6,218,413 B1 | 4/2001 | Hester et al. |
| 6,251,869 B1 | 6/2001 | Bohanon |
| 6,265,178 B1 | 7/2001 | Martin, Jr. |
| 6,281,210 B1 | 8/2001 | Hester, Jr. |
| 6,294,201 B1 | 9/2001 | Kettelhoit et al. |
| 6,458,793 B1 | 10/2002 | Warner et al. |
| 6,805,881 B1 | 10/2004 | Kanikanti et al. |
| 6,818,243 B2 | 11/2004 | Nagashima et al. |
| 7,034,017 B2 | 4/2006 | Straub et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,157,456 B2 | 1/2007 | Straub et al. |
| 2001/0029351 A1 | 10/2001 | Falotico et al. |
| 2001/0046987 A1 | 11/2001 | Hester et al. |
| 2003/0153610 A1 | 8/2003 | Straub et al. |
| 2003/0161882 A1 | 8/2003 | Waterman |
| 2004/0162427 A1 | 8/2004 | Rosentreter et al. |
| 2004/0242660 A1 | 12/2004 | Straub et al. |
| 2005/0064006 A1 | 3/2005 | Perzborn et al. |
| 2005/0182055 A1 | 8/2005 | Berwe et al. |
| 2005/0261502 A1 | 11/2005 | Rosentreter et al. |
| 2006/0154969 A1 | 7/2006 | Rosentreter et al. |
| 2006/0173047 A1 | 8/2006 | Straub et al. |
| 2006/0258724 A1 | 11/2006 | Straub et al. |
| 2007/0026065 A1 | 2/2007 | Benke et al. |
| 2007/0149522 A1 | 6/2007 | Thomas |
| 2008/0026057 A1 | 1/2008 | Benke |
| 2008/0090815 A1 | 4/2008 | Straub et al. |
| 2008/0200674 A1 | 8/2008 | Straub et al. |

FOREIGN PATENT DOCUMENTS

AU     744002      2/2002

(Continued)

OTHER PUBLICATIONS

Bono, F., et al., "Human Umbilical Vein Endothelial Cells Express High Affinity Receptors for Factor Xa", Journal of Cellular Physiology, 1997, vol. 172, pp. 36-43.

(Continued)

*Primary Examiner* — Kamal A Saeed
(74) *Attorney, Agent, or Firm* — Connolly Bove Lodge & Hutz, LLP

(57) ABSTRACT

The present application relates to novel 2-aminoethoxyacetic acid derivatives, to processes for their preparation, to their use for the treatment and/or prophylaxis of diseases and also to their use for preparing medicaments for the treatment and/or prophylaxis of diseases, in particular thromboembolic disorders.

8 Claims, No Drawings

FOREIGN PATENT DOCUMENTS

| | | |
|---|---|---|
| DE | 2836305 A1 | 3/1979 |
| DE | 196 04 223 A1 | 8/1997 |
| DE | 19962924 A1 | 7/2001 |
| DE | 10105989 | 9/2001 |
| DE | 10105989 | 8/2002 |
| DE | 10129725 A1 | 1/2003 |
| DE | 10355461 A1 | 6/2005 |
| EP | 0 127 902 A2 | 12/1984 |
| EP | 0 316 594 A1 | 5/1989 |
| EP | 0 352 781 A2 | 1/1990 |
| EP | 0350002 A1 | 1/1990 |
| EP | 0623615 A1 | 11/1994 |
| EP | 0645376 A1 | 3/1995 |
| EP | 0738726 A1 | 10/1996 |
| EP | 0 785 200 A2 | 7/1997 |
| EP | 0930076 A1 | 7/1999 |
| EP | 0950386 A2 | 10/1999 |
| GB | 2140687 | 12/1984 |
| WO | WO-93/09103 A1 | 5/1993 |
| WO | WO-93/23384 A1 | 11/1993 |
| WO | WO-97/03072 A1 | 1/1997 |
| WO | WO-97/09328 A1 | 3/1997 |
| WO | WO-97/10223 A1 | 3/1997 |
| WO | WO-98/01446 A1 | 1/1998 |
| WO | WO-98/54161 A1 | 12/1998 |
| WO | WO-99/02525 A1 | 1/1999 |
| WO | WO-99/03846 A1 | 1/1999 |
| WO | WO-99/06371 A1 | 2/1999 |
| WO | WO-99/21535 A1 | 5/1999 |
| WO | WO-99/24428 A1 | 5/1999 |
| WO | WO-99/29688 A1 | 6/1999 |
| WO | WO-99/31092 A1 | 6/1999 |
| WO | WO-99/37304 A1 | 7/1999 |
| WO | WO-99/37630 A1 | 7/1999 |
| WO | WO-99/37641 A1 | 7/1999 |
| WO | WO-99/40094 A1 | 8/1999 |
| WO | WO-99/59616 A1 | 11/1999 |
| WO | WO-00/16748 A1 | 3/2000 |
| WO | 0147919 | 5/2001 |
| WO | WO-01/42242 A1 | 6/2001 |
| WO | WO-01/44212 A1 | 6/2001 |
| WO | WO-01/46185 A1 | 6/2001 |
| WO | WO-01/47949 A1 | 7/2001 |
| WO | WO-0147919 | 7/2001 |
| WO | WO-02/25210 A1 | 3/2002 |
| WO | WO-02/064575 A1 | 8/2002 |
| WO | WO-02/070484 A1 | 9/2002 |
| WO | WO-02/070485 A1 | 9/2002 |
| WO | WO-02/070520 A1 | 9/2002 |
| WO | WO-02/079195 A1 | 10/2002 |
| WO | WO-02/079196 A1 | 10/2002 |
| WO | WO-03/000256 A1 | 1/2003 |
| WO | WO-03/008384 A1 | 1/2003 |
| WO | WO-03/035133 A1 | 5/2003 |
| WO | WO-03/053441 A1 | 7/2003 |
| WO | WO-2004/060887 A1 | 7/2004 |
| WO | WO-2005/060940 A1 | 5/2005 |
| WO | WO-2005/068456 A1 | 7/2005 |
| WO | WO-2006/072367 A1 | 7/2006 |
| WO | WO-2006/079474 A1 | 8/2006 |
| WO | WO-2007/036306 A1 | 4/2007 |
| WO | WO-2007/039122 A2 | 4/2007 |
| WO | WO-2007/039132 A1 | 4/2007 |
| WO | WO-2007/039134 A1 | 4/2007 |
| WO | WO-2007/042146 A1 | 4/2007 |
| WO | WO-2008/012002 A1 | 1/2008 |
| WO | WO-2008/052671 A1 | 5/2008 |

OTHER PUBLICATIONS

Cocks, T. M., et al., "Protease-Activated Receptors: Sentries for Inflammation", Tips, 2000, vol. 21, pp. 103-108.
Ross, R., "Atherosclerosis—An Inflammatory Disease", New England J. of Medicine, 1999, vol. 340, No. 2, pp. 115-126.
Nakata, M., et al., "DX9065a an Xa Inhibitor, Inhibits Prothrombin-Induced A549 Lung Adenocarcinoma Cell Proliferation", Cancer Letters, 1998, vol. 122, pp. 127-133.
Kaiser, B., et al., "A Synthetic Inhibitor of Factor Xa, DX-9065a, Reduces Proliferation of Vascular Smooth Muscle Cells in Vivo in Rats", Thrombosis Research, 2000, vol. 98, pp. 175-185.
Altieri, D. C., et al., "Identification of Effector Cell Protease Receptor-1", The Journal of Immunology, 1990, vol. 145, No. 1, pp. 246-253.
Coughlin, S. R., "Thrombin Signalling and Protease-Activated Receptors", Nature, 2000, vol. 407, pp. 258-264.
Ornstein, D. L., et al., "Cancer, Thrombosis, and Anticoagulants", Current Opinion in Pulmonary Medicine, 2000, vol. 6, pp. 301-308.
Dabbagh, K., et al., "Thrombin Stimulates Smooth Muscle Cell Procollagen Synthesis and mRNA Levels via a PAR-1 Mediated Mechanism", Thrombasis and Haemostasis, vol. 79, No. 2 1997, pp. 405-409.
Herault, J-P., et al., "Activation of Human Vascular Endothelial Cells by Factor Xa: Effect of Specific Inhibitors", Biochemical Pharmacology, 1999, vol. 57, pp. 603-610.
Leveugle, B., et al., "Heparin Oligosaccharides that Pass the Blood-Brain Barrier Inhibit—Amyloid Precursor Protein Secretion and Heparin Binding to □-Amyloid Peptide", Journal of Neurochemistry, 1998, vol. 70, No. 2, pp. 736-744.
Molino, M., et al., "Differential Expression of Functional Protease-Activated Receptor-2 (PAR-2) in Human Vascular Smooth Muscle Cells", Arteriosclerosis, Thrombasis, and Vascular Biology, vol. 18, No. 5, 1998, pp. 825-832.
Plescia, J., et al., "Activation of MAC-1 (CD11b/CD18)-Bound Factor X by Release Cathepsin G Defines an Alternative Pathway of Leucocyte Initiation of Coagulation", Biochem. J., 1996, vol. 319, pp. 873-879.
Howells, G. L., et al., "Proteinase-Activated Receptor-2: Expression by Human Neutrophils", Journal of Cell Science, 1997, vol. 110, pp. 881-887.
Herbert, J.-M., et al., "Effector Protease Receptor 1 Mediates the Mitogenic Activity of Factor Xa for Vascular Smooth Muscle Cells in Vitro and In Vivo", J. Clin. Invest., 1998, vol. 101, No. 5, pp. 993-1000.
Donnelly, K. M., et al., "*Ancylostoma caninum* Anticoagulant Peptide Blocks Metastasis In Vivo and Inhibits Factor Xa Binding to Melanoma Cells In Vitro", Thromb Haemost, 1998, vol. 79, pp. 1041-1047.
Ragosta, M., et al., "Specific Factor Xa Inhibition Reduces Restenosis After Balloon Angioplasty of Atherosclerotic Femoral Arteries in Rabbits", Circulation, 1994, vol. 89, No. 3, pp. 1262-1271.
Zhang, Y., et al., "Tissue Factor Controls the Balance of Angiogenic and Antiangiogenic Properties of Tumor Cells in Mice", J. Clin. Invest., 1994, vol. 94, pp. 1320-1327.
Green, D., et al., "Lower Mortality in Cancer Patients Treated with Low-Molecular-Weight Versus Standard Heparin", The Lancet, 1992, vol. 339, p. 1476.
Ko, F. N., et al., "Coagulation Factor Xa Stimulates Platelet-Derived Growth Factor Release and Mitogenesis in Cultured Vascular Smooth Muscle Cells of Rat", J. Clin. Invest., 1996, vol. 98, No. 6, pp. 1493-1501.
Kakkar, A. K., et al., "Antithrombotic Therapy in Cancer", BMJ, 1999, vol. 3318, pp. 1571-1572.
Gasic, G. P., et al., "Coagulation Factors X, Xa, and Protein S as Potent Mitogens of Cultured Aortic Smooth Muscle Cells", Proc. Natl. Acad. Sci. USA, 1992, vol. 89, pp. 2317-2320.
Cirino, G., et al., "Factor Xa as an Interface Between Coagulation and Inflammation: Molecular Mimicry of Factor Xa Association with Effector Cell Protease Receptor-1 Induces Acute Inflammation In Vivo", J. Clin. Invest., 1997, vol. 99, No. 10, pp. 2446-2451.
Senden, N. H. M., et al., "Factor Xa Induces Cytokine Production and Expression of Adhesion Molecules by Human Umbilical Vein Endothelial Cells", The Journal of Immunology, 1998, vol. 161, pp. 4318-4324.
Papapetropoulos, A., et al., "Hypotension and Inflammatory Cytokine Gene Expression Triggered by Factor Xa-Nitric Oxide Signaling", Proc. Natl. Acad. Sci. USA, 1998, vol. 95, pp. 4738-4742.

Camerer, E., et al., "Tissue Factor- and Factor X-dependent Activation of Protease-Activated Receptor 2 by Factor VIIa", PNAS, 2000, vol. 97, No. 10, pp. 5255-5260.

Donovan, F. M., et al., "Thrombin Induces Apoptosis in Cultured Neurons and Astrocytes via a Pathway Requiring Tyrosine Kinase and RhaA Activities", The Journal of Neuroscience, 1997, vol. 17, No. 14, pp. 5316-5326.

Lindner, J. R., et al., "Delayed Onset of Inflammation in Protease-Activated Receptor-2-Deficient Mice", The Journal of Immunology, 2000, pp. 6504-6510.

Bouchard, B. A., et al., "Effector Cell Protease Receptor-1, a Platelet Activation-dependent Membrane Protein, Regulates Prothrombinase-catalyzed Thrombin Generation", The Journal of Biological Chemistry, 1997, vol. 272, No. 14, pp. 9244-9251.

Molino, M., et al., "Endothelial Cell Thrombin Receptors and PAR-2", The Journal of Biological Chemistry, 1997, vol. 272, No. 17, pp. 11133-11141.

Nicholson, A. C., et al., "Effector Cell Protease Receptor-1 Is a Vascular Receptor for Coagulation Factor Xa", The Journal of Biological Chemistry, 1996, vol. 271, No. 45, pp. 28407-28413.

Watson, D. J., et al., "Heparin-Binding Properties of the Amyloidogenic Peptides A and Amylin", The Journal of Biological Chemistry, 1997, vol. 272, No. 50, pp. 31617-31624.

Tuszynski, G. P., et al., "Isolation and Characterization of Antistasin", The Journal of Biological Chemistry, 1987, vol. 262, No. 20, pp. 9718-9723.

Kranzhöfer, R., et al., "Thrombin Potently Stimulates Cytokine Production in Human Vascular Smooth Muscle Cells but Not in Mononuclear Phagocytes", Circulation Research, 1996, vol. 79, No. 2, pp. 286-294.

Schwartz, R. S., et al., "Neointimal Thickening After Severe Coronary Artery Injury is Limited by Short-term Administration of a Factor Xa Inhibitor", Circulation, 1996, vol. 93, No. 8, pp. 1542-1548.

Abendschein, D. R., et al., "Inhibition of Thrombin Attenuates Stenosis After Arterial Injury in Minipigs", JACC, 1996, vol. 28, No. 7, pp. 1849-1855.

Carmeliet, P., et al., "Gene Manipulation and Transfer of the Plasinogen and Coagulation System in Mice", Seminars in Thrombosis and Hemostasis, 1996, vol. 22, No. 6, pp. 525-542.

Stouffer, G. A., et al., "The Role of Secondary Growth Factor Production in Thrombin-Induced Proliferation of Vascular Smooth Muscle Cells", Seminars in Thrombosis and Hemostasis, 1998, vol. 24, No. 2, pp. 145-150.

Bevilacqua, M. P., et al., "Inducible Endothelial Functions in Inflammation and Coagulation", Seminars in Thrombosis and Hemostasis, 1987, vol. 13, No. 4, pp. 425-433.

Riedl, B., et al., "Recent Developments with Oxazolidinone Antibiotics", Exp. Opin. Ther. Patents, 1999, vol. 9, No. 5, pp. 625-633.

Barbachyn, M.R., et al., "Identification of Novel Oxazolidinone (U-100480) with Potent Antimycobacterial Activity", J. Med. Chem., 1996, vol. 39, pp. 680-685.

Tucker, J. A., et al, "Piperazinyl Oxazolidinone Antibacterial Agents Containing a Pyridine, Diazene, or Triazene Heteroaromatic Ring", J. Med. Chem. 1998, vol. 41, pp. 3727-3735.

Brickner, S.J., et al., "Synthesis and Antibacterial Activity of U-100592 and U-100766, Two Oxazolidinone Antibacterial Agents for the Potenial treatment of Multidrug-Resistant Gram-Positive Bacterial Infections" J. Med. Chem., 1996, vol. 39, pp. 673-679.

Gregory, W.A., et al., "Antibacterials. Synthesis and Structure-Activity Studies of 3-Aryl-2-oxooxazolidines. 1. The "B" Group", J. Med. Chem., 1989, vol. 32, No. 8, pp. 1673-1681.

Berry, C. N., et al., "Antithrombotic Actions of Argatroban in Rat Models of Venous, 'Mixed' and Arterial Thrombosis, and its Effects on the Tail Transection Bleeding Time", Br. J. Pharmacol., 1994, vol. 113, pp. 1209-1214.

Meng, K., et al., "Effect of Acetylsalicylic Acid of Experimentally Induced Arterial Thrombosis in Rats", Naunyn-Schmiedeberg's Arch. Pharmacol.,1977, vol. 301, pp. 115-119.

Chern, J.W., et al., "Studies on Quinazolines IX:[1] Fluorination Versus 1,2-Migration on the Reaction of 1,3-Bifunctionalized Amino-2-Propanol with DAST", Tetrahedron Lett., 1998, vol. 39, pp. 8483-8486.

Shakespeare, W. C., et al., "Palladium-Catalyzed Coupling of Lactams with Bromobenzenes", Tetrahedron Lett., 1999, vol. 40, pp. 2035*2038.

Renger, B., et al., "Direkte N-Arylierung von Amiden: Eine Verbesserung der Goldberg-Reaktion", Synthesis, 1985, pp. 856-860.

Aebischer, E., et al., "Synthesis of N-Arylrolipram Derivatives—Potent and Selective Phosphodiesterase-IV Inhibitors—by Copper Catalyzed Lactam-Aryl Halide Coupling", Hetercycles, 1998, vol. 48, No. 11 , pp. 2225-2229.

Pfeil, E., et al., "β-Aminoäthylierung von Indol und 2-methylindol", Angew Chem., 1967, vol. 79, No. 4, pp. 188-189.

Ziegler, C. B., et al., "Synthesis of Some Novel 7-Substituted Quinolonecarboxylic Acids via Nitroso and Nitrone Cycloadditions", J. Hetercycl. Chem., 1988, vol. 25, No. 2, pp. 719-723.

Bartoli, G., et al, "Electronic and Steric Effects in Nucleophilic Aromatic Substitution. Reaction by Phenoxides as Nucleophiles in Dimethyl Sulfoxide", J. Org. Chem., 1975, vol. 40, No. 7, pp. 872-874.

Reppe, et al., "N-p-Merthoxyphenyl-pyrrolidon", Justus Liebigs Ann. Chem., 1955 vol. 596, p. 208.

Luvalle, J.E., et al., "Oxidation Processes. XXI.[1] The Autoxidation of the ρ-Phenylenediamines", J. Am. Chem. Soc., 1948, vol. 70, pp. 2223-2233.

Snyder, H.R., et al., "Imidazo[4,5f]quinolines III: Antibacterial 7-Methyl-9-(substituted Arylamino)imidazo[4,5-☐]quinolines", J. Pharm. Sci., 1977, vol. 66, pp. 1204-1406.

Adams, R., et al., "Sulfanilamide Derivatives. I", J. Am. Chem. Soc. 1939, vol. 61, pp. 2342-2349.

Khanna, I.K. , et al., "1,2-Diarylpyrroles as Potent and Selective Inhibitors of Cyclooxygenase-2", J. Med. Chem., 1997, vol. 40 , pp. 1619-1633.

Gutcait, A., et al., "Studies on Quinazolines. 6.[1] Asymmetric Synthesis of (S)-(+)- and (R)-(−)-3-[[4-(2-Methoxyphenyl)piperazin-1-yl]methylthio-2,3,-dihydromidazo[1,2-c]quinazolines", Tetrahedron Asym., 1996, vol. 7, No. 6, pp. 1641-1648.

Grell, W., et al., "Repaglinide and Related Hypoglycemic Benzoic Acid Derivatives", J. Med. Chem., 1998, vol. 41, pp. 5219-5246.

Artico, M. et al., "Rsearch on Compounds with Antiblastic Activity", Farmaco Ed. Sci. 1969, vol. 24, pp. 179-190.

Dankwardt, S. M., et al., "Nonpeptide Bradykinin Antagonist Analogs based on a Model of a Sterling-Winthrop Nonpeptide Bradykinin Antagonist Overlapped with Cyclic Hexapeptide Bradykinin Antagonist Peptides", Bioorg. Med. Chem. Lett., 1997, vol. 7, No. 14, pp. 1921-1926.

Reppe, et al., "N-6-Aminohexyl-pyrrolidon", Justus Liebigs Ann. Chem. 1955, vol. 596, pp. 204.

Bouchet, P., et al., "σValues of N-Substitutes Azoles", J. Chem. Soc. Perkin Trans., 1974, vol. 2, pp. 449-451.

Surrey, A. R., et al., "The Preparation of N-Benzyl-3-Morpholones and N-Benzyl-3-Homomorpholones from N-(Hydroxyalkyl)-chloroacetamides" J. Amer. Chem. Soc., 1955, vol. 77, pp. 633-636.

Tong, L.K.J., et al., "The Mechanism of Dye Formation in Color Photography. VII. Intermediate Bases in the Deamination of Quinonediimines" J. Amer. Chem. Soc. 1960, vol. 82, 1988-2001.

Delande, S.A., "Heterocycles", Chemical Abstracts, American Chemical Society, 1979, vol. 90, pp. 663.

Bots, M., et al., Coagulation and Fibrinolysis Markers and Risk of Dementia, Haemostasis, vol. 28 (1998); pp. 216-222.

Benzakour, O., et al., "Cellular and molecular events in atherogenesis; basis for pharmacological and gene therapy approaches to stenosis," Cellular Pharmacology, 1996, vol. 3, pp. 7-22.

Kanthou, C., et al., "Cellular effects of thrombin and their signalling pathways," Cellular Pharmacology, vol. 2 (1995); pp. 293-302.

Kaiser, B., et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.

Tyrrell, D., et al., "Heparin in Inflammation: Potential Therapeutic Applications Beyond Anticoagulation," Advances in Pharmacology, vol. 46 (1999); pp. 151-208.

Smirova, I., et al., "Thrombin Is an Extracellular Signal that Activates Intracellular Death Protease Pathways Inducing Apoptosis in Model Motor Neurons," J. Neurobiology, vol. 36 (1998); pp. 64-80.

Bono, F., et al., "Factor Xa Activates Endothelial Cells by a Receptor Cascade Between EPR-1 and PAR-2," Arterioscler Thromb Vasc Biol., Nov. 2000; pp. 1-6.

Lala, P. et al, "Role of Nitric Oxide in tumor progression: Lessons Learned from Experimental Tumors," *Cancer and Metastasis Review*, vol. 17, pp. 91-106 (1998).

Golub, T., et al., *Molecular Classification of Cancer Science* (1999), vol. 286, 531-537.

FDA mulls drug to slow late-stage Alzheimer's [online], [retrieved on Sep. 23, 2003]. Retrieved from the internet, URL:http://www.cnn.com/2003/HEALTH/conditions/09/24/alzheimers.drug.ap/index.html>.

Ulllman's Encyclopedia of Industrial Chemistry, Fifth Revised Ed., Editors: Elvers, B., Hawkins, S., VCH Verlagsgesellschaft mbH, Weinheim, 19985-1996, Ch. 5, 488-506.

Zhu, B., Scarborough, R., "Recent Advances in Inhibitors of Factor Xa in the Prothrombinase Complex," *Curr. Opinions Card. Pul. Ren. Inv. Drugs*, 1:63-87 (1999).

Uzan, A., "Antithrombotic Agents," *Emerging Drugs: The Prospect for Improved Medicines*, 3: 189-208 (1998).

Kaiser, B., "Thrombin and Factor Xa Inhibitors," *Drugs of the Future*, 23: 423-426 (1998).

Al-Obeidi, F., Ostrem, J., "Factor Xa Inhibitors," *Expert Opin. Therapeutic Patents*, 9: 931-953 (1999).

Al-Obeidi, F., Ostrem, J., "Factor Xa Inhibitors by Classical and Combinatorial Chemistry," *DDT*, 3: 223-231 (May 1998).

Hauptmann, J.,et al., "Synthetic Inhibitors of Thrombin and Factor Xa: From Bench to Bedside," *Thrombosis Research*, 93: 203-241 (1999).

Pschyrembel, Klinisches Worterbuch, 257. Auflage, 1994, Walter de Gruyter Verlag, p. 199-200, Stichwort "Blutgerinnung."

Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.

Pschyrembel, Klinisches Worterbuch, 257. Auflage, 1994, Walter de Gruyter Verlag, p. 610, Stichwort "Heparin."

Rompp Lexikon Chemie, Ver. 1.5, 1998, Georg Thieme Verlag Stuttgart, Stichwort "Heparin."

Pschyrembel, Klinisches Worterbuch, 257. Auflage, 1994, Walter de Gruyter Verlag, p. 292, Stichwort "Cumarinderivate."

Becker, M.R., et al., "Synthesis, Sar and in Vivo Activity of Novel Thienopyridine Sulfonamide Pyrrolidininones as Factor Xa Inhibitors," *Bioorganic and Medicinal Chemistry Letters*, 9: 2753-2758 (1999).

Linder, J., et al., "Delayed Onset of Inflammation in Protease-Activated Receptor-2-Deficient Mice," J. Immunology, 2000, pp. 6504-6510.

Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, Sep. 22, 2005, pp. 5900-5908.

Caira, M. Crystalline Polymorphism of Organic Compounds. Springer Verlag Berlin Heidelberg 198, 1998, pp. 163-208.

Hancock, B. et al. Characteristics and Significance of the Amorphous State in Pharmaceutical Systems. Journal of Pharmaceutical Science. 86, 1 (Jan. 1997), pp. 1-12.

Chiou, W.L. et al. Pharmaceutical Applications of Solid Dispersion Systems. Journal of Pharmaceutical Sciences 60, (1971). 128-1302.

Ford, J.L. The Current Status of Solid Dispersions. Pharm Acta Helv. 61, (1986)69-88.

Rasenack, N. et al. Poorly Water-soluble Drugs for Oral Delivery—A Challenge for Pharmaceutical Development. Pharmazeutische Industrie 67, Nr. 5 (2005), 583-591.

Breitenbach, J. Melt extrusion: from process to drug delivery technology. European Journal of Pharmaceutics and Biopharmaceutics 54 (2002) 107-117.

Breitenbach, J. Feste Loesungen durch Schmelzextrusion—ein integriertes Herstellkonzept. Pharmazie in unserer Zeit 29 (2000), 46-49.

http://familydoctor.org/online/famdocen/home/common/heartdisease/basics/290.html.

Kubitza, et al., Multiple dose escalation study Investigating the pharmacodyanamics, safety, and pharmacokinetics of BAY 59-7939 an oral, direct Factor Xa inhibitor in healthy male subjects, Blood, vol. 102:11: Nov. 16, 2003, p. 811a.

Kubitza, et al., Abstract 3010, Single dose escalation study investigating the pharmacodyanamlcs, safety, and pharmacokinetics of BAY 59-7939 an oral, direct Factor Xa inhibitor in healthy male subjects, Blood, vol. 102:11. Nov. 16, 2003, p. 813a.

Lerk, et al., Effect of Hydrophilization Drugs on Release Rat from Capsules, J. of Pharma. Sciences, 67(7), pp. 935-939 (1978).

Lerk, et al., In Vitro and In Vivo Availability of Hydrophilized Phenytoin from Capsules, J. of Pharma. Sciences, 68(5), pp. 634-638 (1979).

Greaves, et al., Novel Approaches to the Preparation of Low-Dose Solid Dosage Forms,Pharmaceutical Technology. January, pp. 60-64, (1995).

Reppe, et al., Justus Liebigs Ann. Chem. 596, 1955, p. 209.

Wong et al., The Journal of Pharmacology and Expermental Therapeutics, vol. 295, No. 1 (2000) pp. 212-218.

[Database Bielstein] Bielstein Institute for Organic Chemistry, Frankfurt-Main, DE. Database Accession No. 8822985.

Perzborn, E. et al. In vitro and in vivo studies of the novel antithrombotic agent BAY 59-7939-an oral, direct Factor Xa inhibitor. Journal of Thrombosis and Haemostasis 3, Mar. 3, 2005, pp. 514-521.

Espinosa, G. et al. Thrombotic microangiopathic haemolytic anaemia and antiphospholipid antibodies. Annals of the Rheumatic Diseases, 63, Jun. 6, 2004, pp. 730-736.

Bonomini, V. et al. A New Antithrombotic Agent in the Treatment of Acute Renal Failure Due to Hemolytic-Uremic Syndrome and Thrombotic Thrombocytopenic Purpura. Nephron 37, 1984, 2, 144.

Sinha, U. et al. Antithrombotic and hemostatic capacity of factor Xa versus thrombin inhibitors in models of venous and arteriovenous thrombosis. European Journal of Pharmacology 2000, 395, 51-59.

Betz, A. Recent advances in Factor Xa inhibitors. Expert Opinion Ther. Patents 2001, 11, 1007-1017.

Tan, K.T. et al. Factor X inhibitors. Expert Opinion Investig. Drugs 2003, 12, 799-804.

Ruef, J. et al. New antithrombotic drugs on the horizon. Expert Opinion Investig. Drugs 2003, 12, 781-797.

Samama, M.L. Synthetic direct and indirect factor Xa inhibitors. Thrombois Research 2002, 106, V267-V273.

Quan, M.L. The race to an orally active Factor Xa inhibitor: Recent advances. Current Opinion in Drug Discovery & Development 2004, 7, 460-469.

The Ephesus Study, Blood 2000, 96, 490a.

The Penthifra Study, Blood 2000, 96, 490a.

The Pentamaks Study, Blood 2000, 96, 490a-491a.

The Pentathlon 2000 Study, Blood 2000, 96, 491a.

Leadley, R.J. Coagulation Factor Xa Inhibition: Biological Background and Rationale. Current Topics in Medical Chemistry 2001, 1, 151-159.

Gilligan, D.M. et al. The Management of Atrial Fibrillation. The American Journal of Medicine, vol. 101, (4) 1996, 413-421.

Kubitza, D. et al. Novel factor Xa inhibitors for prevention and treatment of thromboembolic diseases. Expert Opinion on Investig. Drugs, vol. 15, (8) 2006, pp. 843-855.

Williams, E.M. Vaughan. Classificating anti-arrhythimic drugs. In: Cardiac Arrythias—Proceedings of a symposium, sandoe E., soedertaeje: Astra (1970), pp. 449-469.

Braunwald et al., "Heart Disease: A Textbook of Cardiovascular Medicine", 5th Ed., W.B. Saunders Company, 1997. (preface and index).

Pschyrembel, Klinisches Wörterbuch (transl: Clinical Dictionary), Walter de Gruyter Verlag, 1994, p. 610 (heparin definition).

Rompp online Lexikon Chemie (transl.: Chemical Dictionary), Heparin definition, Georg Thieme Verlag, Stuttgart, 1998.

Hirsh et al., "Oral Anticoagulants: Mechanism of Action, Clinical Effectiveness, and Optimal Therapeutic Range," Chest, 2001, vol. 119, pp. 8S-21S.

Ansell et al., "Managing Oral Anticoagulant Therapy," Chest, 2001, vol. 119, pp. 22S-38S.

Wells et al., "Interactions of Warfarin with Drugs and Food", Ann, Internal. Med. 1994, vol. 121, pp. 676-683.

Hauptmann et al., "Synthetic Inhibitors of Thrombin and Factor Xa: From Bench to Bedside", Thrombosis Research, 1999, vol. 93, pp. 203-241.

Raghavan et al., "Recent advances in the status and targets of antithrombotic agents", Drugs of the Future, 2002, vol. 27, No. 7, pp. 669-683.

Wieland et al., "Approaches in anticoagulation: Rationales for target positioning", Current Opinion in Investigational Drugs, 2003, vol. 4, No. 3, pp. 264-271.

Ries et al., "Serine Proteases as Targets for Antithrombotic Therapy", Drugs of the Future, 2003, vol. 28, No. 4, pp. 355-370.

Linkins et al., "New Anticoagulant Therapy", Annu. Rev. Med., 2005, vol. 56, pp. 63-77.

Walenga et al., "Factor Xa Inhibitors: Today and Beyond", Current Opinion in Investigatinal Drugs, 2003, vol. 4, No. 3, pp. 272-281.

Ruef et al., "New Antithrombotic Drugs on the Horizon", Expert Opin. Investig, Drugs 2003, vol. 12, No. 5, pp. 781-797.

Quan et al., "The Race to an Orally Active Factor Xa Inhibitor: Recent Advances", Current Opinion in Drug Discovery & Development, 2004, vol. 7, No. 4, pp. 460-469.

International Search Report and Written Opinion of the International Search Authority for PCT/EP2006/008949, Dec. 12, 2006.

Observations Under Article 115 EPC, submitted anonymously to EPO on Dec. 23, 2010 in EP 1928867 A1.

Cirino, G. et al. Inflammation-Coagulation Network: Are Serine Protease Receptors the Knot?; Tips; 2000, vol. 21, pp. 170-172.

2-AMINOETHOXYACETIC ACID DERIVATIVES AND THEIR USE

The present application relates to novel 2-aminoethoxyacetic acid derivatives, to processes for their preparation, to their use for the treatment and/or prophylaxis of diseases and also to their use for preparing medicaments for the treatment and/or prophylaxis of diseases, in particular thromboembolic disorders.

Blood coagulation is a protective mechanism of the organism which helps to "seal" defects in the wall of the blood vessels quickly and reliably. Thus, loss of blood can be avoided or kept to a minimum. Hemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here factor Xa, which is formed from the proenzyme factor X, plays a key role, since it connects the two coagulation paths. The activated serine protease Xa cleaves prothrombin to thrombin. The resulting thrombin, in turn, cleaves fibrinogen to fibrin. Subsequent crosslinking of the fibrin monomers causes formation of blood clots and thus hemostasis. In addition, thrombin is a potent effector of platelet aggregation which likewise contributes significantly to hemostasis.

Hemostasis is subject to a complex regulatory mechanism. Uncontrolled activation of the coagulant system or defective inhibition of the activation processes may cause formation of local thrombi or embolisms in vessels (arteries, veins, lymph vessels) or in heart cavities. This may lead to serious thromboembolic disorders. In addition, in the case of consumption coagulopathy, hypercoagulability may—systemically—result in disseminated intravascular coagulation. Thromboembolic complications furthermore occur in microangiopathic hemolytic anemias, extracorporeal blood circulation, such as hemodialysis, and also in connection with prosthetic heart valves.

Thromboembolic disorders are the most frequent cause of morbidity and mortality in most industrialized countries. [Heart Disease: A Textbook of Cardiovascular Medicine, Eugene Braunwald, 5th edition, 1997, W.B. Saunders Company, Philadelphia].

The anticoagulants, i.e. substances for inhibiting or preventing blood coagulation, which are known from the prior art, have various, often grave disadvantages. Accordingly, in practice, an efficient treatment method or prophylaxis of thromboembolic disorders is very difficult and unsatisfactory.

In the therapy and prophylaxis of thromboembolic disorders, use is firstly made of heparin, which is administered parenterally or subcutaneously. Owing to more favorable pharmacokinetic properties, preference is nowadays more and more given to low-molecular-weight heparin; however, even with low-molecular-weight heparin, it is not possible to avoid the known disadvantages described below, which are involved in heparin therapy. Thus, heparin is ineffective when administered orally and has only a relatively short half-life. Since heparin inhibits a plurality of factors of the blood coagulation cascade at the same time, the action is nonselective. Moreover, there is a high risk of bleeding; in particular, brain hemorrhages and gastrointestinal bleeding may occur, which may result in thrombopenia, drug-induced alopecia or osteoporosis [Pschyrembel, Klinisches Wörterbuch, 257th edition, 1994, Walter de Gruyter Verlag, page 610, entry "Heparin"; Römpp Lexikon Chemie, Version 1.5, 1998, Georg Thieme Verlag Stuttgart, entry "Heparin"].

A second class of anticoagulants are the vitamin K antagonists. These include, for example, 1,3-indanediones, and especially compounds such as warfarin, phenprocoumon, dicumarol and other coumarin derivatives which inhibit the synthesis of various products of certain vitamin K-dependent coagulation factors in the liver in a nonselective manner. Owing to the mechanism of action, however, the onset of the action is very slow (latency to the onset of action 36 to 48 hours). It is possible to administer the compounds orally; however, owing to the high risk of bleeding and the narrow therapeutic index, a time-consuming individual adjustment and monitoring of the patient are required [J. Hirsh, J. Dalen, D. R. Anderson et al., "Oral anticoagulants: Mechanism of action, clinical effectiveness, and optimal therapeutic range" *Chest* 2001, 119, 8S-21S; J. Ansell, J. Hirsh, J. Dalen et al., "Managing oral anticoagulant therapy" *Chest* 2001, 119, 22S-38S; P. S. Wells, A. M. Holbrook, N. R. Crowther et al., "Interactions of warfarin with drugs and food" *Ann. Intern. Med.* 1994, 121, 676-683].

Recently, a novel therapeutic approach for the treatment and prophylaxis of thromboembolic disorders has been described. This novel therapeutic approach aims to inhibit factor Xa. Because of the central role which factor Xa plays in the blood coagulation cascade, factor Xa is one of the most important targets for anticoagulants [J. Hauptmann, J. Stürzebecher, *Thrombosis Research* 1999, 93, 203; S. A. V. Raghavan, M. Dikshit, "Recent advances in the status and targets of antithrombotic agents" *Drugs Fut.* 2002, 27, 669-683; H. A. Wieland, V. Laux, D. Kozian, M. Lorenz, "Approaches in anticoagulation: Rationales for target positioning" *Curr. Opin. Investig. Drugs* 2003, 4, 264-271; U. J. Ries, W. Wienen, "Serine proteases as targets for antithrombotic therapy" *Drugs Fut.* 2003, 28, 355-370; L.-A. Linkins, J. I. Weitz, "New anticoagulant therapy" *Annu. Rev. Med.* 2005, 56, 63-77 (online publication August 2004)].

It has been shown that, in animal models, various both peptidic and nonpeptidic compounds are effective as factor Xa inhibitors. A large number of direct factor Xa inhibitors is already known [J. M. Walenga, W. P. Jeske, D. Hoppensteadt, J. Fareed, "Factor Xa Inhibitors: Today and beyond" *Curr. Opin. Investig. Drugs* 2003, 4, 272-281; J. Ruef, H. A. Katus, "New antithrombotic drugs on the horizon" *Expert Opin. Investig. Drugs* 2003, 12, 781-797; M. L. Quan, J. M. Smallheer, "The race to an orally active Factor Xa inhibitor: Recent advances" *Curr. Opin. Drug Discovery & Development* 2004, 7, 460-469]. Non-peptidic factor Xa inhibitors having an oxazolidinone core structure are described in WO 01/047919 and WO 02/064575.

It is an object of the present invention to provide novel substances for controlling disorders, in particular thromboembolic disorders, which substances have improved solubility in water and physiological media.

The present invention provides compounds of the general formula (I)

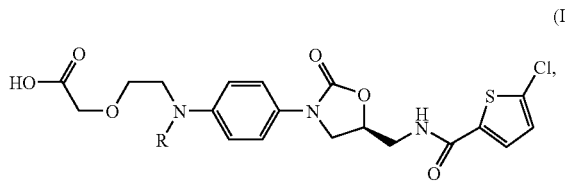

in which
R represents hydrogen, $(C_1-C_6)$-alkyl, $(C_1-C_6)$-alkanoyl, $(C_1-C_6)$-alkoxycarbonyl, mono- or di-$(C_1-C_6)$-alkylaminocarbonyl, benzoyl or heteroaroyl, where
  benzoyl and heteroaroyl for their part may be substituted by halogen, cyano, $(C_1-C_4)$-alkyl or $(C_1-C_4)$-alkoxy,
and salts, solvates and solvates of the salts thereof.

Compounds according to the invention are the compounds of the formula (I) and their salts, solvates and solvates of the salts, the compounds, comprised by formula (I), of the formulae mentioned below and their salts, solvates and solvates of the salts and the compounds, comprised by the formula (I), mentioned below as embodiments and their salts, solvates and solvates of the salts if the compounds, comprised by formula (I), mentioned below are not already salts, solvates and solvates of the salts.

Depending on their structure, the compounds according to the invention can exist in stereoisomeric forms (enantiomers, diastereomers). Accordingly, the invention comprises the enantiomers or diastereomers and their respective mixtures. From such mixtures of enantiomers and/or diastereomers, it is possible to isolate the stereoisomerically uniform components in a known manner.

If the compounds according to the invention can be present in tautomeric forms, the present invention comprises all tautomeric forms.

In the context of the present invention, preferred salts are physiologically acceptable salts of the compounds according to the invention. The invention also comprises salts which for their part are not suitable for pharmaceutical applications, but which can be used, for example, for isolating or purifying the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalene disulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are those forms of the compounds according to the invention which, in solid or liquid state, form a complex by coordination with solvent molecules. Hydrates are a specific form of the solvates where the coordination is with water. In the context of the present invention, preferred solvates are hydrates.

Moreover, the present invention also comprises prodrugs of the compounds according to the invention. The term "prodrugs" includes compounds which for their part may be biologically active or inactive but which, during the time they spend in the body, are converted into compounds according to the invention (for example metabolically or hydrolytically).

In the context of the present invention, unless specified differently, the substituents have the following meanings:

In the context of the invention, $(C_1-C_6)$-alkyl and $(C_1-C_4)$-alkyl represent a straight-chain or branched alkyl radical having 1 to 6 and 1 to 4 carbon atoms, respectively. Preference is given to a straight-chain or branched alkyl radical having 1 to 4 carbon atoms. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

In the context of the invention, $(C_1-C_6)$-alkoxy and $(C_1-C_4)$-alkoxy represent a straight-chain or branched alkoxy radical having 1 to 6 and 1 to 4 carbon atoms, respectively. Preference is given to a straight-chain or branched alkoxy radical having 1 to 4 carbon atoms. The following radicals may be mentioned by way of example and by way of preference: methoxy, ethoxy, n-propoxy, isopropoxy, n-butoxy and tert-butoxy.

In the context of the invention, $(C_1-C_6)$-alkanoyl [$(C_1-C_6)$-acyl] represents a straight-chain or branched alkyl radical having 1 to 6 carbon atoms which carries a doubly attached oxygen atom in the 1-position and is attached via the 1-position. Preference is given to a straight-chain or branched alkanoyl radical having 1 to 4 carbon atoms. The following radicals may be mentioned by way of example and by way of preference: formyl, acetyl, propionyl, n-butyryl, isobutyryl and pivaloyl.

In the context of the invention, $(C_1-C_6)$-alkoxycarbonyl represents a straight-chain or branched alkoxy radical having 1 to 6 carbon atoms which is attached via a carbonyl group. Preference is given to a straight-chain or branched alkoxycarbonyl radical having 1 to 4 carbon atoms in the alkoxy group. The following radicals may be mentioned by way of example and by way of preference: methoxycarbonyl, ethoxycarbonyl, n-propoxycarbonyl, isopropoxycarbonyl and tert-butoxycarbonyl.

In the context of the invention, mono-$(C_1-C_6)$-alkylamino represents an amino group having a straight-chain or branched alkyl substituent having 1 to 6 carbon atoms. Preference is given to a straight-chain or branched monoalkylamino radical having 1 to 4 carbon atoms. The following radicals may be mentioned by way of example and by way of preference: methylamino, ethylamino, n-propylamino, isopropylamino, n-butylamino, isobutylamino and tert-butylamino.

In the context of the invention, di-$(C_1-C_6)$-alkylamino represents an amino group having two identical or different straight-chain or branched alkyl substituents having in each case 1 to 6 carbon atoms. Preference is given to straight-chain or branched dialkylamino radicals having in each case 1 to 4 carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

In the context of the invention, mono-$(C_1-C_6)$-alkylaminocarbonyl and mono-$(C_1-C_4)$-alkylaminocarbonyl represent straight-chain or branched monoalkylamino radicals having 1 to 6 and 1 to 4 carbon atoms, respectively, which are attached via a carbonyl group. Preference is given to a straight-chain or branched monoalkylaminocarbonyl radical having 1 to 4 carbon atoms in the alkylamino group. The following radicals may be mentioned by way of example and by way of preference: methylaminocarbonyl, ethylaminocarbonyl, n-propylaminocarbonyl, isopropylaminocarbonyl, n-butylaminocarbonyl, isobutylaminocarbonyl and tert-butylaminocarbonyl.

In the context of the invention, di-$(C_1-C_6)$-alkylaminocarbonyl represents a straight-chain or branched dialkylamino radical having in each case 1 to 6 carbon atoms, which is attached via a carbonyl group. Preference is given to straight-chain or branched dialkylaminocarbonyl radicals having in each case 1 to 4 carbon atoms in the alkylamino group. The following radicals may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentyl-aminocarbonyl and N-n-hexyl-N-methylaminocarbonyl.

In the context of the invention, heteroaroyl (heteroarylcarbonyl) represents an aromatic heterocycle (heteroaromatic) having a total of 5 or 6 ring atoms and up to three identical or different ring heteroatoms from the group consisting of N, O and S, which is attached via a carbonyl group. The following radicals may be mentioned by way of example: furoyl, pyrroyl, thienoyl, pyrazoyl, imidazoyl, thiazoyl, oxazoyl, isoxazoyl, isothiazoyl, triazoyl, oxadiazoyl, thiadiazoyl, pyridinoyl, pyrimidinoyl, pyridazinoyl, pyrazinoyl. Preference is given to a 5- or 6-membered heteroaroyl radical having up to two heteroatoms from the group consisting of N, O and S, such as, for example, furoyl, thienoyl, thiazoyl, oxazoyl, isoxazoyl, isothiazoyl, pyridinoyl, pyrimidinoyl, pyridazinoyl, pyrazinoyl.

In the context of the invention, halogen includes fluorine, chlorine, bromine and iodine. Preference is given to fluorine or chlorine.

If radicals in the compounds according to the invention are substituted, the radicals can, unless specified otherwise, be mono- or polysubstituted. In the context of the present invention, the meanings of radicals which occur more than once are independent of one another. Substitution with one, two or three identical or different substituents is preferred. Very particular preference is given to substitution with one substituent.

Preference is given to compounds of the formula (I) in which
R represents hydrogen, methyl, acetyl or represents thienylcarbonyl which may be substituted by chlorine,
and salts, solvates and solvates of the salts thereof.

Preference is also given to compounds of the formula (I) in which
R represents mono-$(C_1-C_4)$-alkylaminocarbonyl,
and salts, solvates and solvates of the salts thereof.

Particular preference is given to compounds of the formula (I) in which
R represents hydrogen, isobutylaminocarbonyl or 5-chloro-2-thienylcarbonyl,
and salts, solvates and solvates of the salts thereof.

Very particular preference is given to the compound according to formula (I) having the following structure:

and salts, solvates and solvates of the salts thereof.

The invention furthermore provides a process for preparing the compounds of the formula (I) according to the invention, characterized in that the compound of the formula (I)

(II)

is converted by selective hydrolysis into the compound of the formula (I-A)

(I-A)

and this is then, in an inert solvent, if appropriate in the presence of a base, reacted with a compound of the formula (III)

$R^A$—X    (III), in which
$R^A$ represents $(C_1-C_6)$-alkyl, $(C_1-C_6)$-alkanoyl, $(C_1-C_6)$-alkoxycarbonyl, di-$(C_1-C_6)$-alkylaminocarbonyl, benzoyl or heteroaroyl, where
  benzoyl and heteroaroyl for their part may be substituted by halogen, cyano, $(C_1-C_4)$-alkyl or $(C_1-C_4)$-alkoxy,
and
X represents a leaving group, such as, for example, halogen, or, if R represents mono-$(C_1-C_6)$-alkylaminocarbonyl, with a compound of the formula (IV)

$R^B$—N=C=O    (IV), in which
$R^B$ represents $(C_1-C_6)$-alkyl,
and the resulting compounds of the formula (I) or (I-A) are, if appropriate, converted with the appropriate (i) solvents and/or (ii) bases or acids into their solvates, salts and/or solvates of the salts.

The hydrolysis in process step (II)→(I-A) is advantageously carried out under acidic conditions. Preferably, a mixture of acetic acid and hydrochloric acid is used for this purpose. The reaction is carried out in a temperature range of from +50° C. to +100° C., preferably at +70° C. The reaction can be carried out at atmospheric, elevated or reduced pressure (for example at from 0.5 to 5 bar). In general, the reaction is carried out at atmospheric pressure.

Inert solvents for the process step (I-A)+(III) or (IV)→(I) are, for example, ethers, such as diethyl ether, tert-butyl methyl ether, dioxane, tetrahydrofuran, glykol dimethyl ether or diethylene glycol dimethyl ether, hydrocarbons, such as benzene, toluene, xylene, hexane, cyclohexane or mineral oil fractions, halogenated hydrocarbons, such as dichloromethane, trichloromethane, carbon tetrachloride, 1,2-dichloroethane, trichloroethylene or chlorobenzene, or other solvents, such as ethyl acetate, acetone, acetonitrile, pyridine, dimethyl sulfoxide, dimethylformamide, N,N'-dimethylpropyleneurea (DMPU), N-methylpyrrolidone (NMP) or, if appropriate, also water. It is also possible to use mixtures of the solvents mentioned. Preference is given to dichloromethane, tetrahydrofuran, dimethylformamide, acetone, water or mixtures of these solvents.

The process step (I-A)+(III) or (IV)→(I) can advantageously be carried out in the presence of a base. Suitable for this purpose are the customary inorganic or organic bases. These preferably include alkali metal hydroxides, such as, for example, lithium hydroxide, sodium hydroxide or potassium hydroxide, alkali metal bicarbonates, such as sodium bicarbonate or potassium bicarbonate, alkali metal or alkaline earth metal carbonates, such as lithium carbonate, sodium carbonate, potassium carbonate, calcium carbonate or cesium carbonate, alkali metal hydrides, such as sodium hydride, amides, such as lithium bis(trimethylsilyl)amide or potassium bis(trimethylsilyl)amide or lithium diisopropylamide, or organic amines, such as triethylamine, N-methylmorpholine, N-methylpiperidine, N,N-diisopropylethylamine, pyridine, 1,5-diazabicyclo-[4.3.0]non-5-ene (DBN), 1,4-diazabicyclo[2.2.2]octane (DABCO®) or 1,8-diazabicyclo[5.4.0]-undec-7-ene (DBU). Particular preference is given to sodium carbonate, potassium carbonate or cesium carbonate, triethylamine, N,N-diisopropylethylamine or pyridine.

The reaction (I-A)+(III) or (IV)→(I) is preferably carried out in a temperature range of from 0° C. to +50° C. The reaction can be carried out at atmospheric, elevated or reduced pressure (for example at from 0.5 to 5 bar). In general, the reaction is carried out at atmospheric pressure.

The compound of the formula (II) and its preparation are described in WO 01/047919 (Example 44). The compounds of the formulae (III) and (IV) are commercially available, known from the literature or can be prepared analogously to processes known from the literature.

The preparation of the compounds according to the invention can be illustrated by the synthesis scheme below:

Scheme

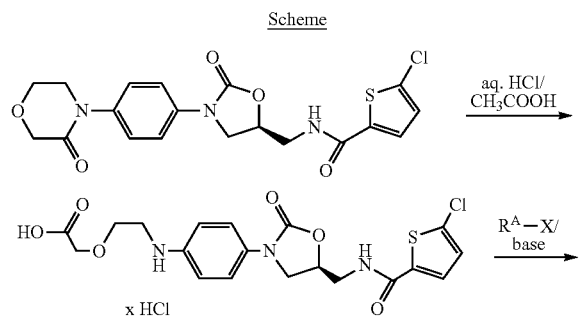

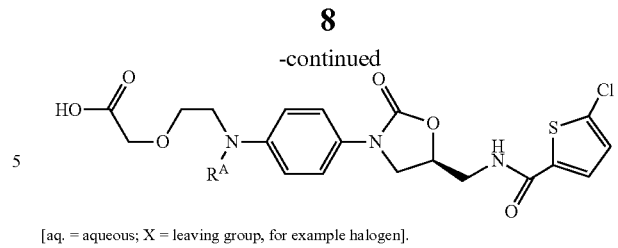

[aq. = aqueous; X = leaving group, for example halogen].

The compounds according to the invention have an unforeseeable useful pharmacological activity spectrum. Accordingly, they are suitable for use as medicaments for the treatment and/or prophylaxis of diseases in humans and animals.

The compounds according to the invention are selective inhibitors of blood coagulation factor Xa which act in particular as anticoagulants. In addition, the compounds according to the invention have favorable physicochemical properties, such as, for example, good solubility in water and physiological media, which is advantageous for their therapeutic application.

The present invention furthermore provides the use of the compounds according to the invention for the treatment and/or prophylaxis of disorders, preferably thromboembolic disorders and/or thromboembolic complications.

For the purposes of the present invention, "thromboembolic disorders" include in particular disorders such as ST-elevation myocardial infarction (STEMI) or non-ST-elevation myocardial infarction (non-STEMI), stable angina pectoris, unstable angina pectoris, reocclusions and restenoses after coronary interventions such as angioplasty or aortocoronary bypass, peripheral areterial occlusive diseases, pulmonary embolisms, deep vein thromboses and kidney vein thromboses, transitory ischemic attacks and also thrombotic and thromboembolic stroke.

Accordingly, the substances are also suitable for preventing and treating cardiogenic thromboembolisms, such as, for example, brain ischemias, stroke and systemic thromboembolisms and ischemias, in patients having acute, intermittent or persistent cardioarrhythmias, such as, for example, atrial fibrillation, and those undergoing cardioversion, furthermore patients having heart valve disorders or having artificial heart valves. In addition, the compounds according to the invention are suitable for treating disseminated intravascular coagulation (DIC).

Thromboembolic complications furthermore occur during microangiopathic hemolytic anemias, extracorporeal blood circulation, such as hemodialysis, and in connection with heart valve prostheses.

Moreover, the compounds according to the invention are also suitable for the prophylaxis and/or treatment of atherosclerotic vascular disorders and inflammatory disorders, such as rheumatic disorders of the locomotor apparatus, and in addition also for the prophylaxis and/or treatment of Alzheimer's disease. Moreover, the compounds according to the invention can be used for inhibiting tumor growth and formation of metastases, for microangiopathies, age-related macular degeneration, diabetic retinopathy, diabetic nephropathy and other microvascular disorders, and also for the prevention and treatment of thromboembolic complications, such as, for example, venous thromboembolisms, in tumor patients, in particular patients undergoing major surgical interventions or chemo- or radiotherapy.

The compounds according to the invention can additionally also be used for preventing coagulation ex vivo, for example for preserving blood and plasma products, for cleaning/pretreating catheters and other medical tools and instruments, for coating synthetic surfaces of medical tools and instruments used in vivo or ex vivo or for biological samples comprising factor Xa.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, using an anticoagulatory effective amount of the compound according to the invention.

The present invention furthermore provides a method for preventing blood coagulation in vitro, in particular in banked blood or biological samples comprising factor Xa, which method is characterized in that an anticoagulatory effective amount of the compound according to the invention is added.

The present invention furthermore provides medicaments comprising a compound according to the invention and one or more further active compounds, in particular for the treatment and/or prophylaxis of the disorders mentioned above. The following compounds may be mentioned by way of example and by way of preference as active compounds suitable for combinations:

lipid-lowering agents, in particular HMG-CoA (3-hydroxy-3-methylglutaryl-coenzyme A) reductase inhibitors;

coronary therapeutics/vasodilators, in particular ACE (angiotensin-converting enzyme) inhibitors; AII (angiotensin II) receptor antagonists; β-adrenoceptor antagonists; alpha-1-adrenoceptor antagonists; diuretics; calcium channel blockers; substances which cause an increase in the cyclic guanosine monophosphate (cGMP) concentration such as, for example, stimulators of soluble guanylate cyclase;

plasminogen activators (thrombolytics/fibrinolytics) and compounds enhancing thrombolysis/fibrinolysis, such as inhibitors of the plasminogen activator inhibitor (PAI inhibitors) or inhibitors of the thrombin-activated fibrinolysis inhibitor (TAFI inhibitors);

anticoagulants;

platelet aggregation-inhibiting substances (platelet aggregation inhibitors, thrombocyte aggregation inhibitors);

fibrinogen receptor antagonists (glycoprotein-IIb/IIIa antagonists);

and also antiarrhythmics.

The present invention furthermore provides medicaments comprising at least one compound according to the invention, usually together with one or more inert nontoxic pharmaceutically acceptable auxiliaries, and their use for the purposes mentioned above.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or otic route, or as implant or stent.

For these administration routes, it is possible to administer the compounds according to the invention in suitable administration forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (uncoated and coated tablets, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbarly) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems, (e.g. patches), milk, pastes, foams, dusting powders, implants or stents.

Preference is given to oral or parenteral administration, in particular oral administration.

The compounds according to the invention can be converted into the stated administration forms. This can take place in a manner known per se by mixing with inert, non-toxic, pharmaceutically suitable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

In general, it has proved advantageous to administer on parenteral administration amounts of from about 0.001 to 1 mg/kg, preferably from about 0.01 to 0.5 mg/kg, of body weight to achieve effective results. The dosage on oral administration is from about 0.01 to 100 mg/kg, preferably about 0.01 to 20 mg/kg, and very particularly preferably 0.1 to 10 mg/kg, of body weight.

It may nevertheless be necessary, where appropriate, to deviate from the amounts mentioned, depending on the body weight, the administration route, the individual response to the active compound, the mode of preparation and the time or interval over which administration takes place. Thus, in some cases it may be sufficient to make do with less than the aforementioned minimal amount, whereas in other cases the upper limit mentioned must be exceeded. In the event of administration of larger amounts, it may be advisable to divide these into a plurality of individual doses over the day.

The invention is illustrated by the working examples below. The invention is not limited to the examples.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

Abbreviations and Acronyms

DMSO dimethyl sulfoxide
ESI electrospray ionization (in MS)
h hour(s)
HPLC high pressure, high performance liquid chromatography
LC-MS liquid chromatography-coupled mass spectrometry
min minute(s)
MS mass spectrometry
NMR nuclear magnetic resonance
RT room temperature
$R_t$ retention time
HPLC Method:

High pressure liquid chromatograph fitted with temperature-controlled column oven, UV detector and data evaluation system; column: Cosmosil 5C18-AR-II 5 μm, 25 cm×4.6 mm; mobile phase A: 1.36 g of potassium dihydrogenphosphate in water is made up to 1 litre and adjusted to pH 2.1 with ortho-phosphoric acid (85% strength); mobile phase B: methanol; gradient: 0 min 30% B→35 min 90% B→40 min 90% B; flow rate: 1 ml/min; temperature of the column oven: 45° C.; UV detection: 250 nm; injection volume: 5.0 μl (test solution: 25 mg of sample in 50 ml of acetonitrile).

LC-MS Method:

Instrument: Micromass Quattro LCZ with HPLC Agilent series 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Starting Materials and Intermediates

Example 1A

5-Chloro-N-({(5S)-2-oxo-3-[4-(3-oxomorpholin-4-yl)phenyl]-1,3-oxazolidin-5-yl}methyl)-thiophene-2-carboxamide

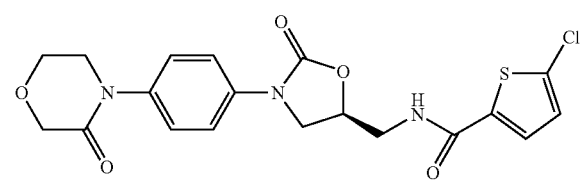

The title compound is prepared by the route described in WO 01/047919 (*Chem. Abstr.* 2001, 135, 92625) under Example 44.

Example 2A

5-Chlorothiophene-2-carbonyl chloride

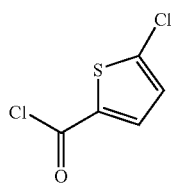

The title compound is prepared by reacting 5-chlorothiophene-2-carboxylic acid with thionyl chloride, see R. Aitken et al., *Arch. Pharm.* (*Weinheim Ger.*) 1998, 331, 405-411.

Working Examples

Example 1

2-({4-[(5S)-5-({[(5-Chloro-2-thienyl)carbonyl]amino}methyl)-2-oxo-1,3-oxazolidin-3-yl]phenyl}-amino)ethoxy]acetic acid hydrochloride

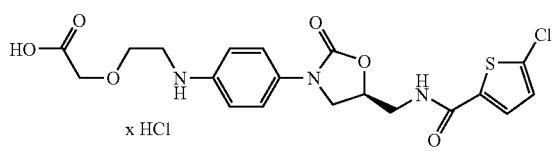

50 g (115 mmol) of 5-chloro-N-({(5S)-2-oxo-3-[4-(3-oxomorpholin-4-yl)phenyl]-1,3-oxazolidin-5-yl}methyl) thiophene-2-carboxamide are suspended in 100 g of acetic acid, 50 g of water and 300 g of 37% strength hydrochloric acid, and the mixture is heated to 70° C. The reaction mixture is stirred at 70° C. for 5-6 h, and after about 2 h a clear solution is formed. The mixture is then cooled to RT, and the resulting suspension is allowed to stand at RT for 15 h. The crystals are filtered off with suction and washed with 40 ml of acetic acid. For further purification, the crystals are twice suspended in each case 150 ml of isopropanol and filtered off with suction and then washed twice with in each case 200 ml of isopropanol. The crystals, which still contain residual moisture, are dried for 15 h at 35° C. and a pressure of <80 mbar.

Yield: 43 g (76% of theory)
HPLC: $R_t$=12.74 min;
MS (ESI): m/z=454 [M+H]$^+$;

$^1$H-NMR (500 MHz, DMSO$_6$): δ=3.39 (m, 2H), 3.60 (m, 2H), 3.71 (m, 2H), 3.85 (m, 1H), 4.10 (s, 2H), 4.15 (m, 1H), 4.82 (m, 1H), 7.20 (d, 1H), 7.27 (br. m, 2H), 7.53 (m, 2H), 7.74 (d, 1H), 9.01 (m, 1H).

Example 2

2-({4-[(5S)-5-({[(5-Chloro-2-thienyl)carbonyl]amino}methyl)-2-oxo-1,3-oxazolidin-3-yl]phenyl}-amino)ethoxy]acetic acid

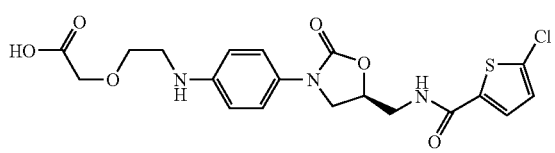

The neutral compound for Example 1 can be prepared by adjusting the aqueous solution of the crude product obtained in Example 1 with triethylamine to pH 7-8, extracting repeatedly with dichloromethane and precipitating the product by adding a little acetic acid. After concentration, the residue is then crystallized from methanol/tert-butyl methyl ether, washed with tert-butyl methyl ether and dried.

Example 3

[2-([(5-Chloro-2-thienyl)carbonyl]{4-[(5S)-5-({[(5-chloro-2-thienyl)carbonyl]amino}methyl)-2-oxo-1,3-oxazolidin-3-yl]phenyl}amino)ethoxy]acetic acid

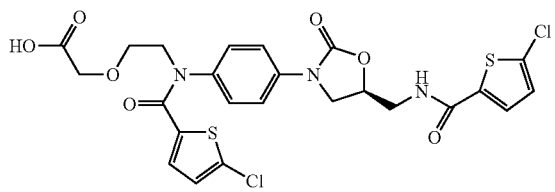

At room temperature, 87 mg (0.63 mmol, 2.1 eq.) of potassium carbonate are added to a suspension of 147 mg (0.30 mmol) of 2-({4-[(5S)-5-({[(5-chloro-2-thienyl)carbonyl]amino}-methyl)-2-oxo-1,3-oxazolidin-3-yl]phenyl}amino)ethoxy]acetic acid hydrochloride in 1.5 ml of water, resulting in the formation of a solution. At room temperature, a solution of 60 mg (0.33 mmol, 1.1 eq.) of 5-chlorothiophene-2-carbonyl chloride in 1.5 ml of acetone is then added dropwise to the reaction mixture, and the mixture is stirred at room temperature for 1 h. The acetone is then removed under reduced pressure and the aqueous residue is adjusted to pH 1 using concentrated hydrochloric acid. The resulting precipitate is filtered off, washed with water and dried under reduced pressure.

Yield: 145 mg (81% of theory)

HPLC: R$_t$=25.93 min;

MS (ESI): m/z=598 [M+H]$^+$;

$^1$H-NMR (400 MHz, DMSO-d$_6$): δ=8.99 (t, 1H), 7.70 (d, 1H), 7.63 (d, 2H), 7.45 (d, 2H), 7.19 (d, 1H), 6.93 (d, 1H), 6.51 (d, 1H), 4.91-4.80 (m, 1H), 4.22 (t, 1H), 3.98 (s, 2H), 3.92-3.84 (m, 3H), 3.67-3.59 (m, 4H).

Example 4

{2-[{4-[(5S)-5-({[(5-Chloro-2-thienyl)carbonyl]amino}methyl)-2-oxo-1,3-oxazolidin-3-yl]phenyl}-(isobutylcarbamoyl)amino]ethoxy}acetic acid

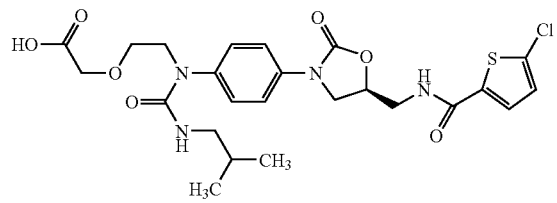

At room temperature, 38 μl (0.22 mmol, 1.1 eq.) of N,N-diisopropylethylamine are added to a suspension of 98 mg (0.20 mmol) of 2-({4-[(5S)-5-({[(5-chloro-2-thienyl)carbonyl]amino}methyl)-2-oxo-1,3-oxazolidin-3-yl]phenyl}amino)ethoxy]acetic acid hydrochloride in 4 ml of tetrahydrofuran, resulting in the formation of a solution. At room temperature, 22 mg (0.22 mmol, 1.1 eq.) of 1-isocyanato-2-methylpropane are then added dropwise to the reaction mixture, and the mixture is stirred overnight. After addition of water and ethyl acetate and phase separation, the aqueous phase is reextracted repeatedly with ethyl acetate. The combined organic phases are dried over sodium sulfate, filtered and concentrated under reduced pressure. The title compound is isolated by preparative RP-HPLC (CromSil C18, acetonitrile/water gradient).

Yield: 19 mg (17% of theory)

LC-MS: R$_t$=3.06 min;

MS (ESI): m/z=553 [M+H]$^+$;

$^1$H-NMR (500 MHz, DMSO-d$_6$): δ=12.59 (br. s, 1H), 8.99 (t, 1H), 7.60 (d, 1H), 7.56 (d, 2H), 7.29 (d, 2H), 7.20 (d, 1H), 5.55 (t, 1H), 4.89-4.80 (m, 1H), 4.20 (t, 1H), 3.99 (s, 2H), 3.85 (dd, 1H), 3.69 (t, 2H), 3.60 (t, 2H), 3.50 (t, 2H), 2.70 (t, 2H), 1.69-1.59 (m, 1H), 0.76 (d, 6H).

B. Evaluation of the Pharmacological Activity

The compounds according to the invention act in particular as selective inhibitors of blood coagulation factor Xa and do not, or only at significantly higher concentrations, inhibit other serine proteases, such as plasmin or trypsin.

Inhibitors of blood coagulation factor Xa are referred to as being "selective" if the IC$_{50}$ values for factor Xa inhibition are smaller by a factor of at least 100 compared with the IC$_{50}$ values for the inhibition of other serine proteases, in particular plasmin and trypsin, where, with a view to the test methods for selectivity, reference is made to the test methods described below of Examples B.a.1) and B.a.2).

The advantageous pharmacological properties of the compounds according to the invention can be determined by the following methods:

a) Test Description (In Vitro)

a.1) Determination of the Factor Xa Inhibition:

The enzymatic action of human factor Xa (FXa) is measured using the conversion of a chromogenic substrate specific for FXa. Factor Xa cleaves p-nitroaniline from the chromogenic substrate. The determinations are carried out in microtiter plates as follows:

The test substances, in various concentrations, are dissolved in DMSO and incubated for 10 minutes at 25° C. with human FXa (0.5 nmol/l dissolved in 50 mmol/l of tris buffer [C,C,C-tris(hydroxymethyl)aminomethane], 150 mmol/l of NaCl, 0.1% BSA [bovine serum albumin], pH=8.3). Pure DMSO is used as control. The chromogenic substrate (150 µmol/l Pefachrome® FXa from Pentapharm) is then added. After an incubation time of 20 minutes at 25° C., the extinction at 405 nm is determined. The extinctions of the test mixtures containing the test substance are compared with the control mixtures without test substance, and the $IC_{50}$ values are calculated from these data.

Activity data from this test are listed in table 1 below:

TABLE 1

| Example No. | $IC_{50}$ [nM] |
|---|---|
| 1 | 32 |
| 3 | 66 |
| 4 | 59 | a.2) Determination of the Selectivity:

To assess selective FXa inhibition, the test substances are examined for their inhibition of other human serine proteases such as trypsin and plasmin. To determine the enzymatic activity of trypsin (500 mU/ml) and plasmin (3.2 nmol/l), these enzymes are dissolved in Tris buffer (100 mmol/l, 20 mmol/l $CaCl_2$, pH=8.0) and incubated with test substance or solvent for 10 minutes. The enzymatic reaction is then started by adding the corresponding specific chromogenic substrates (Chromozym Trypsin® and Chromozym Plasmin®; from Roche Diagnostics) and the extinction at 405 nm is determined after 20 minutes. All determinations are carried out at 37° C. The extinctions of the test mixtures containing test substance are compared with the control samples without test substance, and the $IC_{50}$ values are calculated from these data.

a.3) Determination of the Anticoagulant Action:

The anticoagulant action of the test substances is determined in vitro in human and rabbit plasma. To this end, blood is drawn off in a mixing ratio of sodium citrate/blood of 1:9 using a 0.11 molar sodium citrate solution as receiver. Immediately after the blood has been drawn off, it is mixed thoroughly and centrifuged at about 2500 g for 10 minutes. The supernatant is pipetted off. The prothrombin time (PT, synonyms: thromboplastin time, quick test) is determined in the presence of varying concentrations of test substance or the corresponding solvent using a commercial test kit (Hemoliance® RecombiPlastin, from Instrumentation Laboratory). The test compounds are incubated with the plasma at 37° C. for 3 minutes. Coagulation is then started by addition of thromboplastin, and the time when coagulation occurs is determined. Concentration of test substance which effects a doubling of the prothrombin time is determined.

b) Determination of the Antithrombotic Activity (In Vivo)

b.1) Arteriovenous Shunt Model (Rabbit):

Fasting rabbits (strain: Esd: NZW) are anesthetized by intramuscular administration of Rompun/Ketavet solution (5 mg/kg and 40 mg/kg, respectively). Thrombus formation is initiated in an arteriovenous shunt in accordance with the method described by C. N. Berry et al. [*Semin. Thromb. Hemost.* 1996, 22, 233-241]. To this end, the left jugular vein and the right carotid artery are exposed. The two vessels are connected by an extracorporeal shunt using a vein catheter of a length of 10 cm. In the middle, this catheter is attached to a further polyethylene tube (PE 160, Becton Dickenson) of a length of 4 cm which contains a roughened nylon thread which has been arranged to form a loop, to form a thrombogenic surface. The extracorporeal circulation is maintained for 15 minutes. The shunt is then removed and the nylon thread with the thrombus is weighed immediately. The weight of the nylon thread on its own was determined before the experiment was started. Before extracorporeal circulation is set up, the test substances are administered either intravenously via an ear vein or orally using a pharyngeal tube.

c) Determination of the solubility

Reagents Required:

PBS buffer pH 7.4: 90.00 g of NaCl p.a. (for example from Merck, Art. No. 1.06404.1000), 13.61 g of $KH_2PO_4$ p.a. (for example from Merck, Art. No. 1.04873.1000) and 83.35 g of 1 N NaOH (for example from Bernd Kraft GmbH, Art. No. 01030.4000) are weighed out into a 1 liter measuring flask, the flask is filled with water and the mixture is stirred for about 1 hour;

acetate buffer pH 4.6: 5.4 g of sodium acetate×$3H_2O$ p.a. (for example from Merck, Art. No. 1.06267.0500) are weighed out into a 100 ml measuring flask and dissolved in 50 ml of water, 2.4 g of glacial acetic acid are added, the flask is filled to 100 ml with water, the pH is checked and, if required, adjusted to pH 4.6;

dimethyl sulfoxide (for example from Baker, Art. No. 7157.2500);

distilled water.

Preparation of the Calibration Solutions:

Preparation of the starting solution for calibration solutions (stock solution): about 0.5 mg of the test substance is weighed out accurately into a 2 ml Eppendorf Safe-Lock tube (from Eppendorf, Art. No. 0030 120.094), DMSO is added to a concentration of 600 µg/ml (for example 0.5 mg of substance+833 µl of DMSO) and the mixture is vortexed until complete solution is achieved.

Calibration solution 1 (20 µg/ml): 1000 µl of DMSO are added to 34.4 µl of the stock solution, and the mixture is homogenized.

Calibration solution 2 (2.5 µg/ml): 700 µl of DMSO are added to 100 µl of calibration solution 1, and the mixture is homogenized.

Preparation of the Sample Solutions:

Sample solution for solubilities of up to 10 µl in PBS buffer pH 7.4: about 5 mg of the test substance are weighed out accurately into a 2 ml Eppendorf Safe-Lock tube (from Eppendorf, Art. No. 0030 120.094), and PBS buffer pH 7.4 is added to a concentration of 5 g/l (for example 5 mg of substance+500 µl of PBS buffer pH 7.4).

Sample solution for solubilities of up to 10 µl in acetate buffer pH 4.6: about 5 mg of the test substance are weighed out accurately into a 2 ml Eppendorf Safe-Lock tube (from Eppendorf, Art. No. 0030 120.094), and acetate buffer pH 4.6 is added to a concentration of 5 µl (for example 5 mg of substance+500 µl of acetate buffer pH 4.6).

Sample solution for solubilities of up to 10 µl in water: about 5 mg of the test substance are weighed out accurately into a 2 ml Eppendorf Safe-Lock tube (from Eppendorf, Art. No. 0030 120.094), and water is added to a concentration of 5 g/l (for example 5 mg of substance+500 µl of water).

Practice:

For 24 hours, the sample solutions prepared in this manner are shaken at 1400 rpm using a temperature-controlled shaker (for example the Eppendorf Thermomixer comfort Art. No. 5355 000.011 with interchangeable block Art. No. 5362.000.019) at 20° C. In each case 180 µl are removed from these solutions and transferred into Beckman Polyallomer centrifuge tubes (Art. No. 343621). These solutions are centrifuged at about 223 000×g (for example Beckman Optima L-90K Ultracentrifuge with type 42.2 Ti rotor at 42 000 rpm) for 1 hour. From each sample solution, 100 μl of the supernatant are removed and diluted 1:5, 1:100 and 1:1000 with the respective solvent used (water, PBS buffer 7.4 or acetate buffer pH 4.6). From each dilution, a sample is transferred into a suitable vessel for HPLC analysis.

Analysis:

The samples are analyzed by RP-HPLC. Quantification is carried out using a two-point calibration curve of the test compound in DMSO. The solubility is expressed in mg/l. Analysis sequence: 1) calibration solution 2.5 mg/ml; 2) calibration solution 20 μg/ml; 3) sample solution 1:5; 4) sample solution 1:100; 5) sample solution 1:1000.

HPLC Method for Acids:

Agilent 1100 with DAD (G1315A), quat. pump (G1311A), autosampler CTC HTS PAL, degaser (G1322A) and column thermostat (G1316A); column: Phenomenex Gemini-C18, 50 mm×2 mm, 5μ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degaser (G1322A) and column thermostat (G1316A); column: VDSoptilab Kromasil 100 C18, 60 mm×2.1 mm, 3.5μ; temperature: 30° C.; mobile phase A: water+5 ml perchloric acid/l; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

C. Working Examples of Pharmaceutical Compositions

The compounds according to the invention can be converted into pharmaceutical preparations in the following ways:

Tablet:
Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of the compound according to the invention, lactose and starch is granulated with a 5% strength solution (m/m) of the PVP in water. The granules are dried and then mixed with the magnesium stearate for 5 minutes. This mixture is compressed using a conventional tablet press (see above for the dimensions of the tablet). A compressive force of 15 kN is used as a guideline for the compression.

Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. Stirring is continued until the compound according to the invention has dissolved completely.

i.v. solution:

The compound according to the invention is, at a concentration below saturation solubility, dissolved in a physiologically acceptable solvent (for example isotonic saline, glucose solution 5% and/or PEG 400 solution 30%). The solution is subjected to sterile filtration and filled into sterile and pyrogen-free injection containers.

The invention claimed is:

1. An isolated compound of the formula (I)

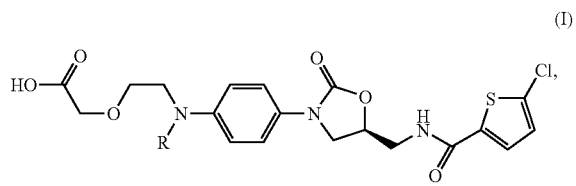

in which

R represents hydrogen, $(C_1-C_6)$-alkyl, $(C_1-C_6)$-alkanoyl, $(C_1-C_6)$-alkoxycarbonyl, mono- or di-$(C_1-C_6)$-alkylaminocarbonyl, benzoyl or heteroaroyl, where benzoyl and heteroaroyl for their part may be substituted by halogen, cyano, $(C_1-C_4)$-alkyl or $(C_1-C_4)$-alkoxy, or a salt thereof.

2. The isolated compound of the formula (I) as claimed in claim 1 in which R is hydrogen, isobutylaminocarbonyl or 5-chloro-2-thienylcarbonyl, or a salt thereof.

3. The isolated compound of the formula (I) as claimed in claim 1 having the structure below:

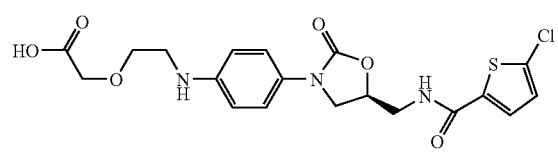

or a salt thereof.

4. A process for preparing the compound of claim 1, characterized in that the compound of the formula (II)

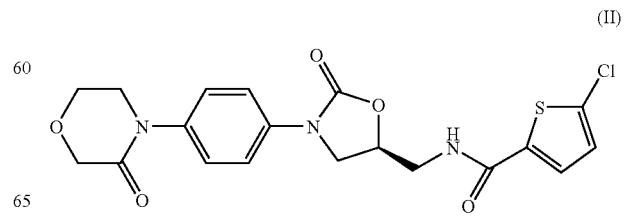

is converted by hydrolysis into the compound of the formula (I-A)

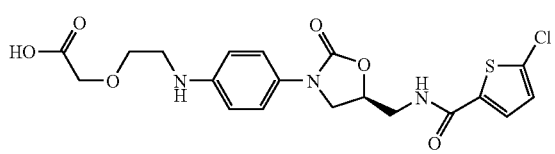
(I-A)

and this is then, in an inert solvent, if appropriate in the presence of a base, reacted with a compound of the formula (III)

$$R^A\!-\!X \qquad (III),$$

in which $R^A$ represents $(C_1\text{-}C_6)$-alkyl, $(C_1\text{-}C_6)$-alkanoyl, $(C_1\text{-}C_6)$-alkoxycarbonyl, di-$(C_1\text{-}C_6)$-alkylaminocarbonyl, benzoyl or heteroaroyl, where benzoyl and heteroaroyl for their part may be substituted by halogen, cyano, $(C_1\text{-}C_4)$-alkyl or $(C_1\text{-}C_4)$-alkoxy, and X represents a leaving group, or, if R represents mono-$(C_1\text{-}C_6)$-alkylaminocarbonyl, with a compound of the formula (IV)

$$R^B\!-\!N\!=\!C\!=\!O \qquad (IV),$$

in which $R^B$ represents $(C_1\text{-}C_6)$-alkyl, and the resulting compound of the formula (I) or (I-A) is isolated and, if appropriate, converted with the appropriate (i) solvent and/or (ii) base or acid into a salt.

5. A pharmaceutical composition comprising the compound of claim 1 in combination with an inert non-toxic, pharmaceutically suitable auxiliary.

6. A pharmaceutical composition comprising the compound in claim 1 in combination with a further active compound.

7. A method for the treatment of thromboembolic disorders in humans and animals, which comprises using administering an anticoagulatory effective amount of at least one compound of claim 1.

8. A method for stabilizing a blood sample in vitro, characterized in that an anticoagulatory effective amount of the compound of claim 1 is added.

* * * * *